US008921578B2

(12) United States Patent
Haley et al.

(10) Patent No.: US 8,921,578 B2
(45) Date of Patent: Dec. 30, 2014

(54) HETEROATOMIC INDENOFLUORENES

(71) Applicant: State of Oregon, acting by and through the State Board of Higher Education on behalf of University of Oregon, Eugene, OR (US)

(72) Inventors: Michael M. Haley, Eugene, OR (US); Daniel T. Chase, Eugene, OR (US)

(73) Assignee: State of Oregan Acting by and Through the State Board of Higher Education on Behalf of the University of Oregan, Eugene, OR (US)

( * ) Notice: Subject to any disclaimer, the term of this patent is extended or adjusted under 35 U.S.C. 154(b) by 0 days.

(21) Appl. No.: 13/712,589

(22) Filed: Dec. 12, 2012

(65) Prior Publication Data

US 2013/0150592 A1 Jun. 13, 2013

Related U.S. Application Data

(60) Provisional application No. 61/569,629, filed on Dec. 12, 2011.

(51) Int. Cl.
*C07D 333/00* (2006.01)
*H01L 51/00* (2006.01)
*C07D 495/04* (2006.01)

(52) U.S. Cl.
CPC ........ *H01L 51/0074* (2013.01); *H01L 51/0094* (2013.01); *C07D 495/04* (2013.01); *Y02E 10/549* (2013.01)
USPC .......................................................... 549/4

(58) Field of Classification Search
USPC .......................................................... 549/4
See application file for complete search history.

(56) References Cited

U.S. PATENT DOCUMENTS

| | | | |
|---|---|---|---|
| 6,690,029 | B1 | 2/2004 | Anthony et al. |
| 7,385,221 | B1 | 6/2008 | Anthony et al. |
| 2008/0220285 | A1 | 9/2008 | Vestweber et al. |
| 2009/0149627 | A1 | 6/2009 | Pan et al. |
| 2013/0096336 | A1 | 4/2013 | Haley et al. |

FOREIGN PATENT DOCUMENTS

| | | |
|---|---|---|
| WO | WO 2010/020329 | 2/2010 |
| WO | WO 2011/159763 | 12/2011 |

OTHER PUBLICATIONS

U.S. Appl. No. 13/704,571, filed Dec. 14, 2012, Haley et al.
Chan et al., "Synthesis, Characterization, and Photovoltaic Properties of Novel Semiconducting Polymers with Thiophene—Phenylene—Thiophene (TPT) as Coplanar Units," *Macromolecules* 41(15):5519-5526, 2008.
Chase et al., "Indeno[1,2-b]fluorenes: Fully Conjugated Antiaromatic Analogues of Acenes," *Angew. Chem. Int. Ed.* 50:1127-1130, 2011.
Miyawaki et al., "Multiple Cycloaromatization of Novel Aromatic Enediynes Bearing a Triggering Device on the Terminal Acetylene Carbon," *Tet. Lett.* 39:6923-6926, 1998.
Padwa et al., "A Comparative Study of the Decomposition of o-Alkylnyl-Substituted Aryl Diazo Ketones. Synthesis of Polysubstituted β-Naphthols via Arylketene Intermediates," *J. Org. Chem.* 58:6429-6437, 1993.
Payne et al., "Stable, Crystalline Acenedithiophenes with up to Seven Linearly Fused Rings," *Organic Letters* 6(19):3325-3328, 2004.
Rose et al., "Synthesis, Crystal Structures and Photophysical Properties of Electron-Accepting Diethynylindenofluorenediones," *Org. Lett.* 13:2106-2106, 2011.
Zhang et al., "Indacenodithiophene Semiconducting Polymers for High-Performance Air-Stable Transistors," *J. Am. Chem. Soc.* 132(33):11437-11439, 2010.
International Search Report and the Written Opinion of the International Searching Authority from International Application No. PCT/US2011/040451 dated Oct. 14, 2011.

*Primary Examiner* — Andrew D Kosar
*Assistant Examiner* — Raymond Covington
(74) *Attorney, Agent, or Firm* — Klarquist Sparkman, LLP Synthesis of *anti*-Diaryl IDTs

(57) ABSTRACT

A compound having a structure of:

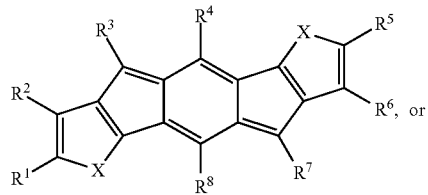
Formula I

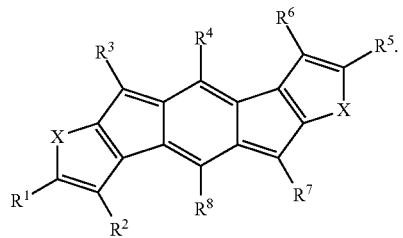
Formula II wherein X is S, SO, SO$_2$, NR$^{10}$, O, or Se;

R$^1$-R$^8$ are each individually H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl, or R$^1$ and R$^2$ together form an aromatic ring and R$^5$ and R$^6$ together form an aromatic ring; and R$^{10}$ is selected from H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl.

22 Claims, 2 Drawing Sheets

HETEROATOMIC INDENOFLUORENES

CROSS-REFERENCE TO RELATED APPLICATION

This application claims the benefit of U.S. Provisional Application No. 61/569,629, which was filed on Dec. 12, 2011, and is incorporated herein by reference in its entirety.

ACKNOWLEDGMENT OF GOVERNMENT SUPPORT

This invention was made with government support under grant NSF CHE-1013032 awarded by the National Science Foundation. The government has certain rights in the invention.

BACKGROUND

Acenes are an exciting class of compounds that have been intensely studied during the past decade. Their alluring optoelectronic properties suggest great potential as the conducting organic material in a variety of device applications such as organic light-emitting diodes (OLEDs), field-effect transistors (OFETs), and solar cells. Pentacene and its derivatives have received the vast amount of attention as this molecule has been hailed as the benchmark for thin film devices. Unfortunately, pentacene readily oxidizes to its respective quinone in aerobic conditions and reacts with itself to afford a butterfly dimer. The driving force for both reactions is the formation of two aromatic naphthalene units which ultimately disrupts overall conjugation and thus leads to poor device performance. While ethynylogation or substitution with thioethers will in general slow degradation, these processes are not completely suppressed.

In addition, in the solid state pentacene packs in an edge-to-face or 'Herring Bone' conformation, which eliminates the possibility of intermolecular π-orbital interactions. Such interactions are crucial for efficient electron transfer, an important characteristic for improving device functionality and performance.

SUMMARY

Disclosed herein are compounds having a structure of:

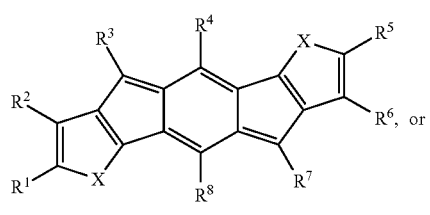

Formula I

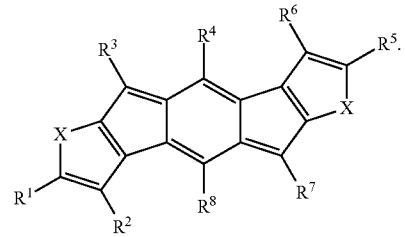

Formula II wherein X is S, SO, $SO_2$, $NR^{10}$, O, or Se;

$R^1$-$R^8$ are each individually H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl, or $R^1$ and $R^2$ together form an aromatic ring and $R^5$ and $R^6$ together form an aromatic ring; and $R^{10}$ is selected from H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl.

Also disclosed herein are electronic or electrooptical devices that include the compounds of Formula I and/or II.

The foregoing will become more apparent from the following detailed description, which proceeds with reference to the accompanying figures.

DETAILED DESCRIPTION

Terminology

Figure 1:
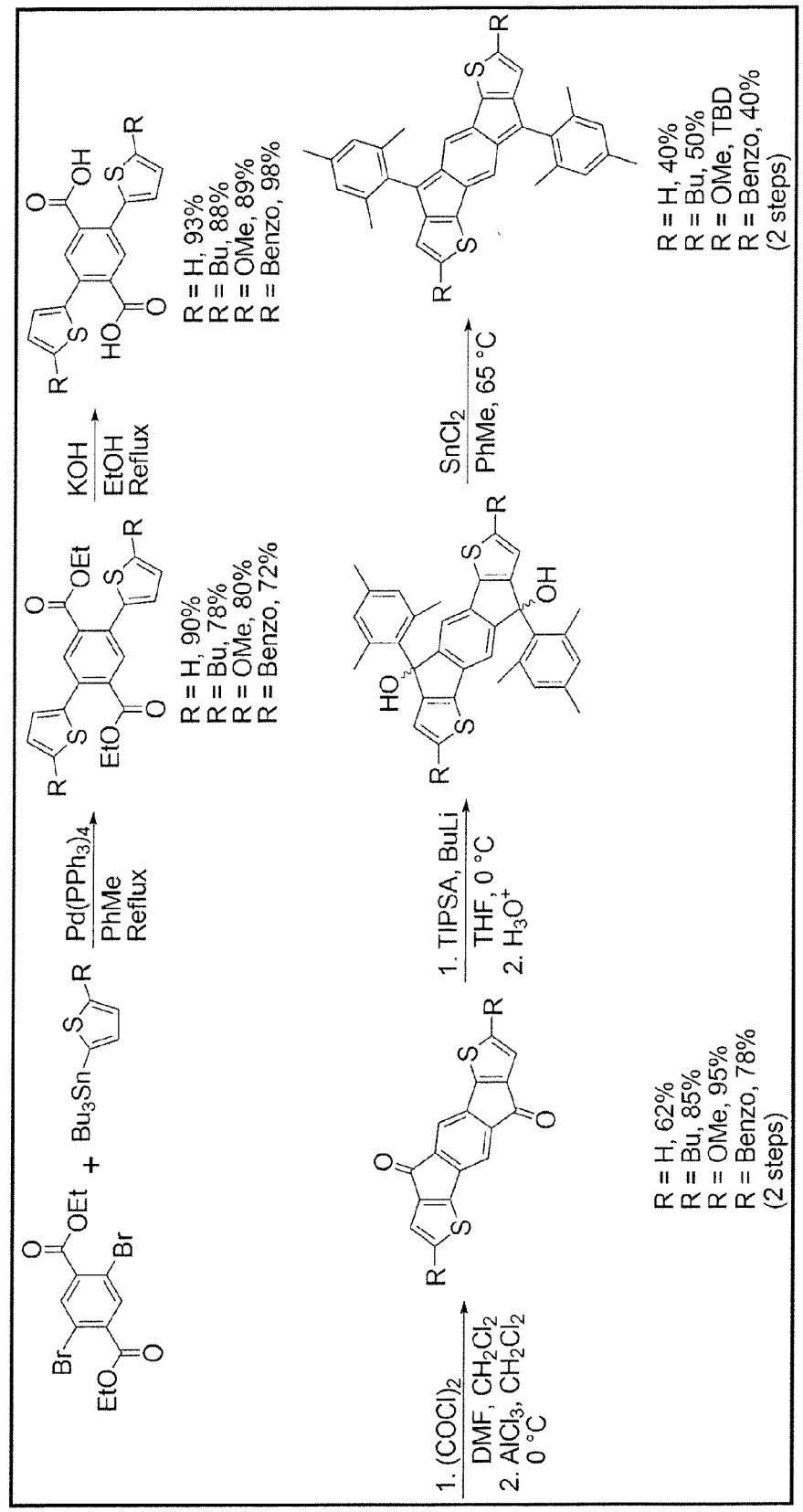
FIG. 1 shows a synthetic scheme for making the compounds disclosed herein.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Also, as used herein, the term "comprises" means "includes."

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, or carboxyl.

The term "alkylaryl" refers to a group in which an alkyl group is substituted for a hydrogen atom of an aryl group. An example is —Ar—R, wherein Ar is an arylene group and R is an alkyl group.

The term "alkynyl" refers to a hydrocarbon group of 2 to 24 carbon atoms and a structural formula containing at least one carbon-carbon triple bond.

The term "alkoxy" refers to a straight, branched or cyclic hydrocarbon configuration and combinations thereof, including from 1 to 20 carbon atoms, preferably from 1 to 10 carbon atoms, more preferably from 1 to 4 carbon atoms, that includes an oxygen atom at the point of attachment. An example of an "alkoxy group" is represented by the formula —OR, where R can be an alkyl group, optionally substituted with, e.g., an alkenyl, alkynyl, aryl, aralkyl, cycloalkyl, halogenated alkyl, or heterocycloalkyl group as described herein.

Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

The term "aralkyl" refers to an alkyl group that has at least one hydrogen atom replaced by an aryl group. An example of an aralkyl group is a benzyl group.

The term "aryl" refers to any carbon-based aromatic group including, but not limited to, phenyl, naphthyl, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous. "Heterocycloalkyl" and "heterocyclic" are used interchangeably herein.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "thioether" refers to a —S—R group, wherein R may be, for example, alkyl (including substituted alkyl), or aryl (including substituted aryl).

The term "thiol" refers to —SH. A "substituted thiol" refers to a —S—R group wherein R is not an aliphatic or aromatic group. For instance, a substituted thiol may be a halogenated thiol such as, for example, —SF$_5$.

Overview

Certain indenofluorenes are known compounds (see, e.g., PCT/US2011/040451). The indeno[1,2-b]fluorene skeleton, a 6-5-6-5-6 fused ring system also known as dibenzo[a,g]-s-indacene, is an attractive alternative structural motif. Every atom in the pentacyclic core unit of a fully conjugated indenofluorene, as disclosed herein, is sp2 hybridized. A fully conjugated indenofluorene should possess some remarkable characteristics: (i) indeno[1,2-b]fluorene compounds have two fewer carbons than pentacene and thus two fewer π-electrons, making indeno[1,2-b]fluorine formally antiaromatic (20 π-electrons); (ii) such molecules host a p-xylylene core, an extremely reactive moiety that typically cannot be isolated due to its tendency to oligomerize/polymerize; and (iii) indenofluorenes do not possess any internal s-cis diene linkages, which should make them resistant to the deleterious cycloaddition pathways that typically degrade pentacenes.

The fully-conjugated heteroatomic indenofluorenes (20 π-electrons) disclosed herein have the same number of aromatic electrons as the core ring structure of indenofluorenes, but the replacement of carbon atoms with heteroatoms in the core ring structure can lower the HOMO-LUMO gap relative to the non-heteroatomic indenofluorenes. In particular, the replacement of the terminal benzene rings of indenofluorene with heteroaromatic rings can alter the absorption wavelength of the compound. For example, in certain indacene-dithiophenes, the adsorption of the indacenedithiophenes is red-shifted relative to the indenofluorene analog. For instance, dimesityl indenofluorene (which is disclosed herein) exhibits an absorption maximum at 516 nm while the corresponding dimesityl indacenedithiophene absorbs at 561 nm. Moreover, a fully conjugated core rings structure as disclosed herein has red-shifted electronic absorptions (smaller band gap) and electrochemical reductions relative to molecules that are not fully conjugated.

Compounds

The heteroatomic indenofluorene compounds may have a structure of:

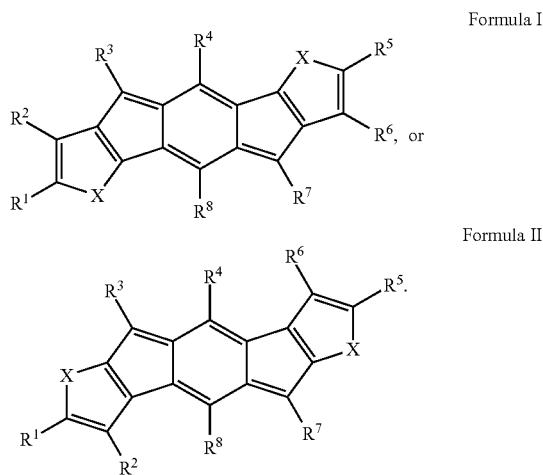

Formula I

Formula II wherein X is S, SO, SO$_2$, NR$^{10}$, O, or Se;

R$^1$-R$^8$ are each individually H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl, or R$^1$ and R$^2$ together form an aromatic ring and R$^5$ and R$^6$ together form an aromatic ring; and R$^{10}$ is selected from H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl.

In certain embodiments, X is S. In certain embodiments, R$^3$ and R$^7$ are each amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl; and R$^1$, R$^2$, R$^4$, R$^5$, R$^6$ and R$^8$ are each H. In certain embodiments, R$^3$ and R$^7$ are each aryl or substituted aryl; and R$^1$, R$^2$, R$^4$, R$^5$, R$^6$ and R$^8$ are each H. In particular, R$^3$ and R$^7$ are each phenyl, alkyl-substituted phenyl (particularly a lower alkyl), alkoxy-substituted phenyl (particularly a lower alkoxy), alkyl- and alkoxy-substituted phenyl (particularly a lower alkyl and a lower alkoxy), haloalkyl-substituted phenyl (particularly a lower haloalkyl or a lower trihaloalkyl), or halo-substituted phenyl (particularly a perhalo-substituted phenyl). In certain embodiments, $R^1$ and $R^5$ are each alkyl (particularly a lower alkyl), alkoxy (particularly a lower alkoxy), or halogen. In certain embodiments, $R^1$ and $R^2$ together form an aromatic ring and $R^5$ and $R^6$ together form an aromatic ring. In certain embodiments, $R^1$ and $R^2$ together form two or more fused aromatic rings and $R^5$ and $R^6$ together form two or more fused aromatic rings. In preferred embodiments, X is S; $R^3$ and $R^7$ are each aryl or substituted aryl, or each alkynyl or substituted alkynyl; $R^1$ and $R^5$ are each H, alkyl (particularly a lower alkyl), alkoxy (particularly a lower alkoxy), halogen, $R^1$ and $R^2$ together form an aromatic ring and $R^5$ and $R^6$ together form an aromatic ring; and the remaining R groups are each H.

Illustrative groups for $R^1$-$R^8$ for Formula 1 or 2 are halogen (e.g., F, Cl, Br), $C_1$-$C_{10}$ alkyl (e.g, methyl, ethyl, propyl, decyl), aryl (e.g, phenyl), substituted alkyl (e.g, halogenated $C_1$-$C_{10}$ alkyl such as —$CF_3$), substituted alkynyl (e.g., silyl-substituted alkynyl such as alkylsilyl-substituted alkynyl (e.g., —C≡C—Si(alkyl)), substituted aryl (e.g, halogenated phenyl such as —$C_6F_5$, 4-$CF_3C_6H_4$, or 3,5-$(CF_3)_2C_6H_3$), alkoxy (e.g., methoxy), a $C_1$-$C_{10}$ alkyl-substituted thiol (e.g., —$SF_5$), thioether (e.g., —SMe or —SBu), a sulfur-containing heteroaryl (e.g, a thienyl), —$NO_2$, —CN, or an alkyl-substituted sulfur-containing heteroaryl (e.g., 2-(5-$BuC_4H_2S$).

The heteroatomic indenofluorenes can be synthesized, for example, as shown in FIG. 1 and below. The synthetic scheme set forth in FIG. 1 and below enables isometric control of the heteroatomic indenofluorenes. Thus, the desired isomers can be synthesized based on the starting reactants and/or reaction conditions without the need for isomeric reaction product mixture separation.

Additional illustrative compounds and reaction schemes are shown below:

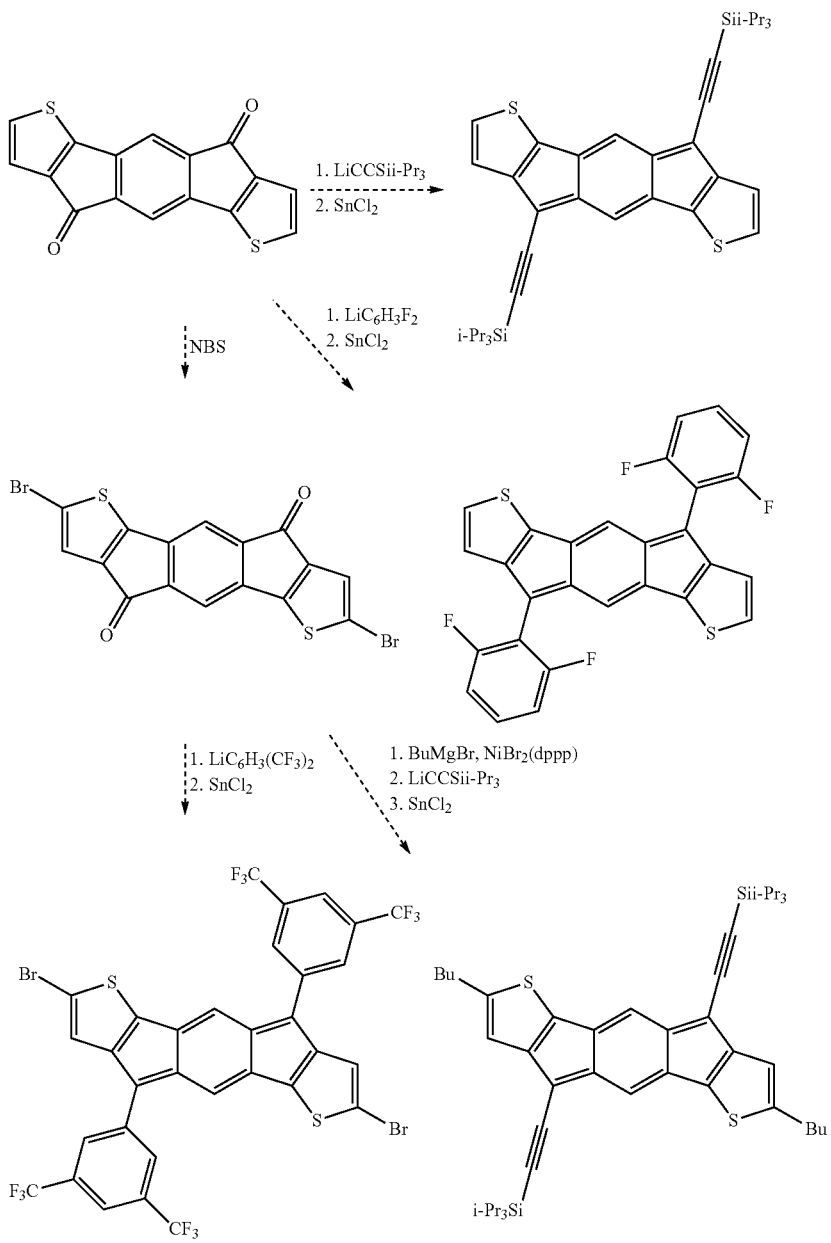

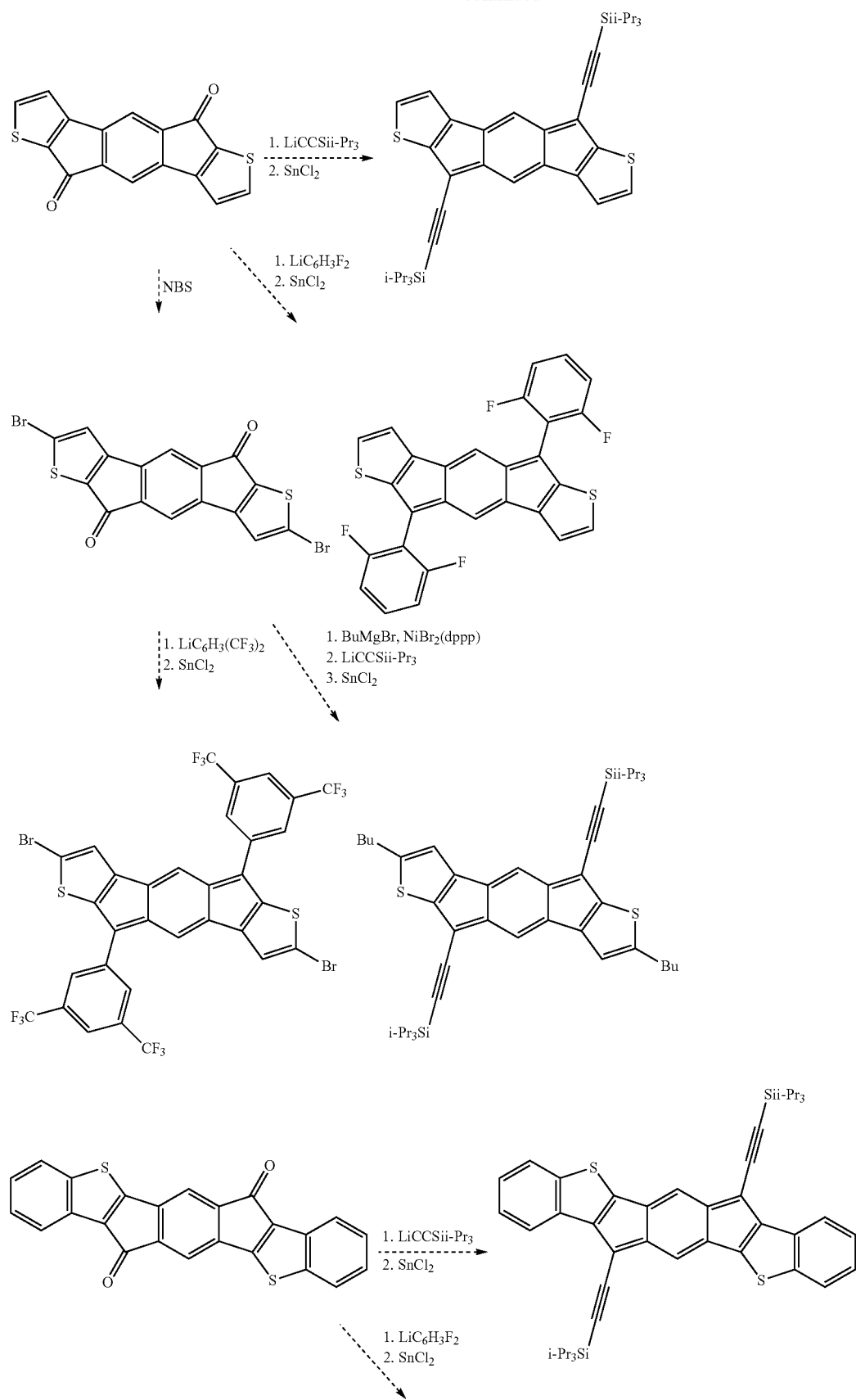

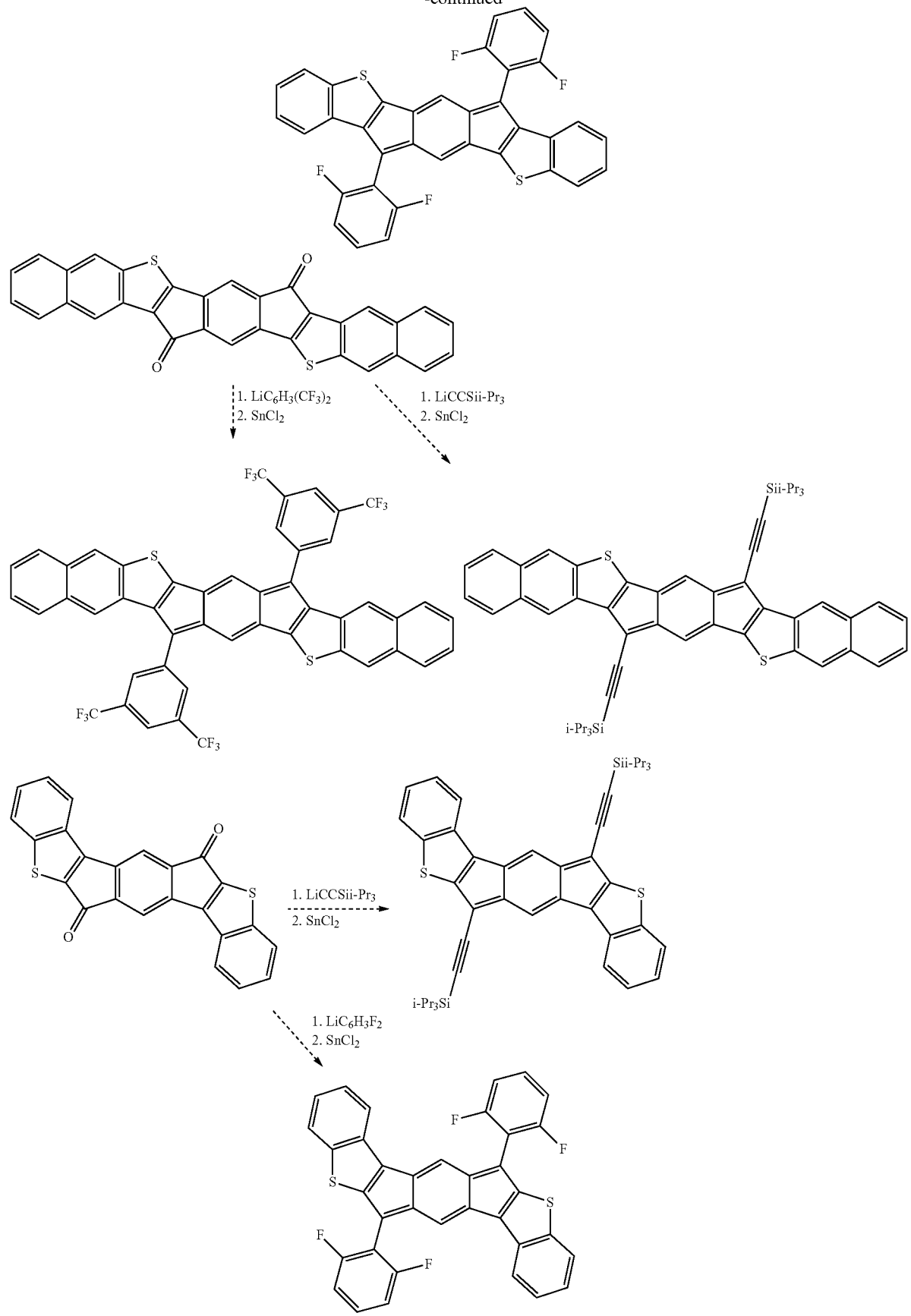

-continued

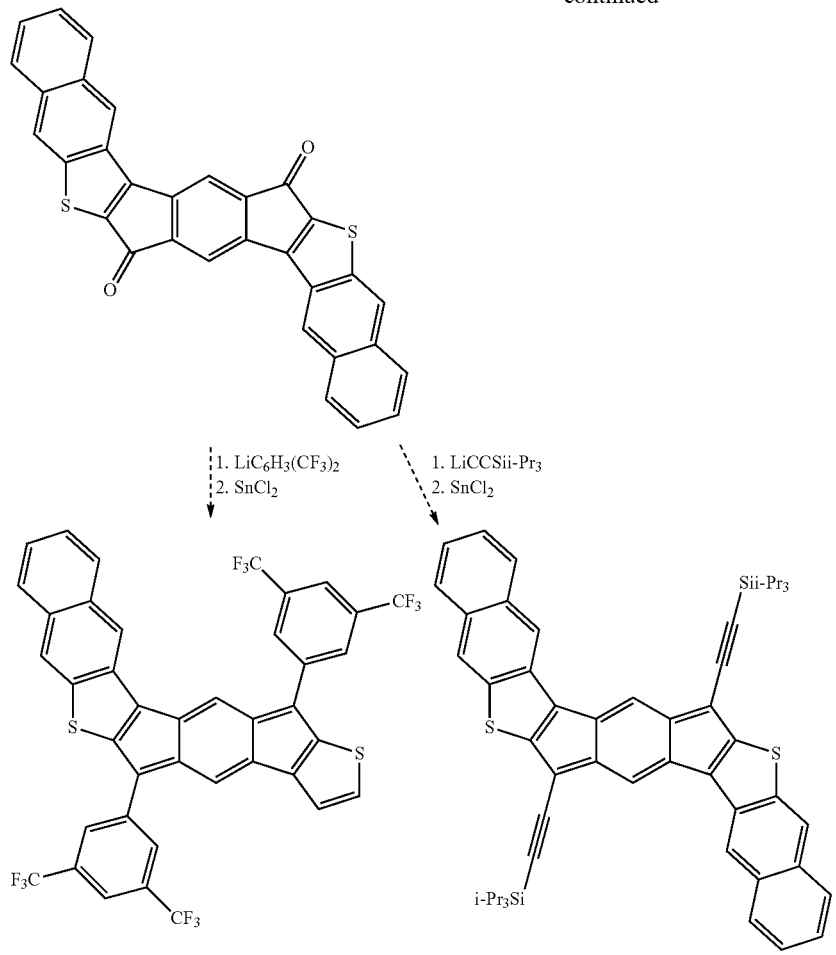

Compound Applications

The heteroaromatic indenofluorene compounds disclosed herein may be used in electronic or electrooptical devices such as, for example, an organic light-emitting diode (OLED), an organic field-effect transistor (OFET), or an organic photovoltaic cell (OPV). The heteroaromatic indenofluorenes disclosed herein may be used as organic semiconductors in form of thin organic layers or films, for example, less than 30 microns thick. For instance, the semiconducting layer is at most 1 micron thick, although it may be thicker if required. For various electronic device applications, the thickness may also be less than about 1 micron thick. For use in an OFET, the layer thickness may typically be 500 nm or less, in an OLEDs be 100 nm or less. The exact thickness of the layer will depend, for example, upon the requirements of the electronic device in which the layer is used.

For example, the active semiconductor channel between the drain and source in an OFET may comprise a layer that includes the indenofluorene. As another example, a hole injection or transport layer, and or an electron blocking layer in an OLED device may comprise a layer that includes the indenofluorene.

An OFET may comprise: a source electrode, a drain electrode, a gate electrode, a semiconducting layer, one or more gate insulator layers, optionally a substrate, wherein the semiconductor layer comprises one or more heteroaromatic indenofluorenes as described herein.

In certain embodiments the photovoltaic cell includes an anode, a cathode, and a semiconductor layer or film that includes at least one of the heteroaromatic indenofluorene compounds disclosed herein.

EXAMPLES

Figure 2:
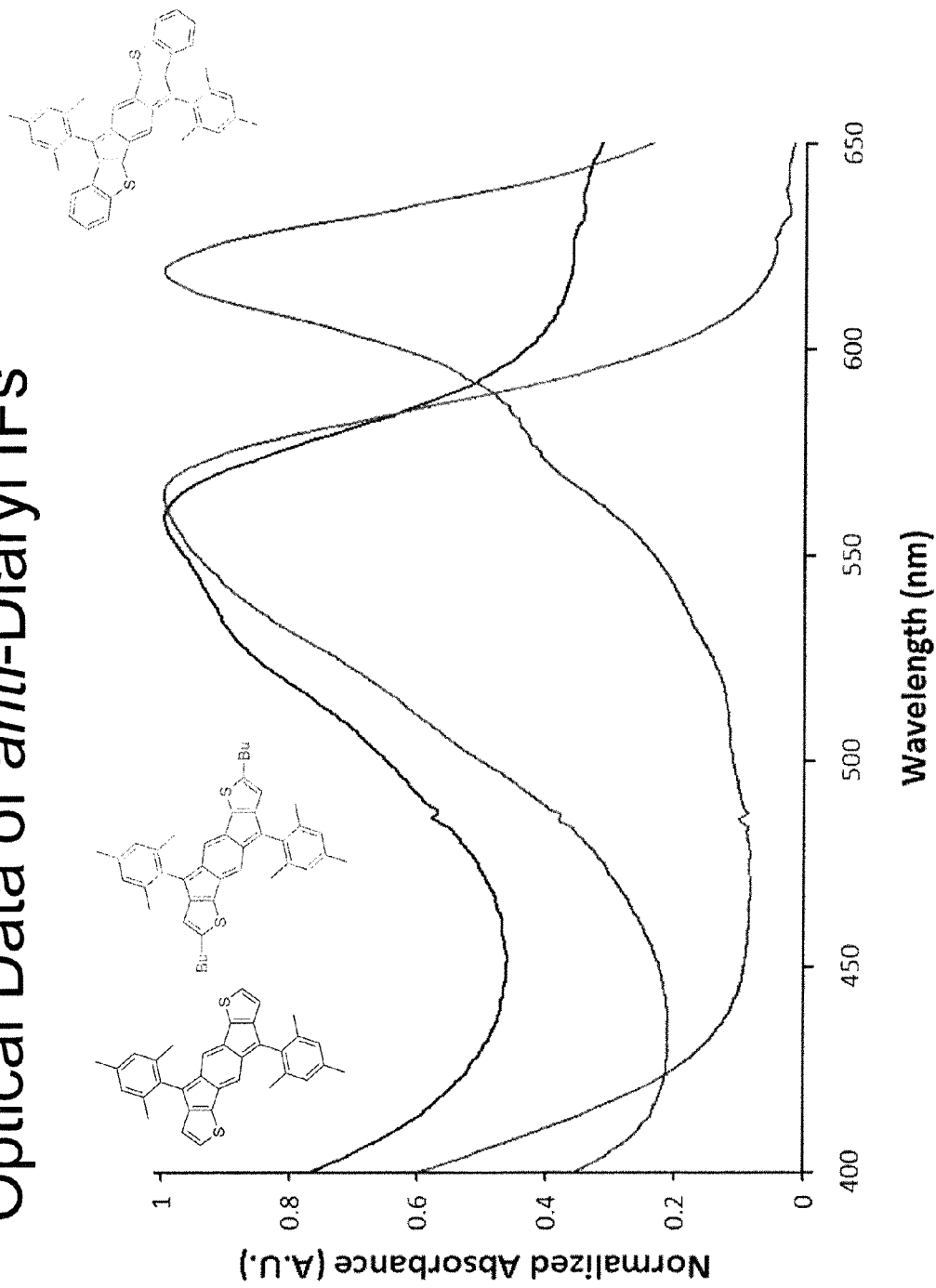
FIG. 2 shows the electronic absorption data for several indacenedithiophenes disclosed herein.

Examples of several heteroaromatic indenofluorenes are shown in FIGS. 1 and 2.

Described below are several synthesis of compounds disclosed herein:

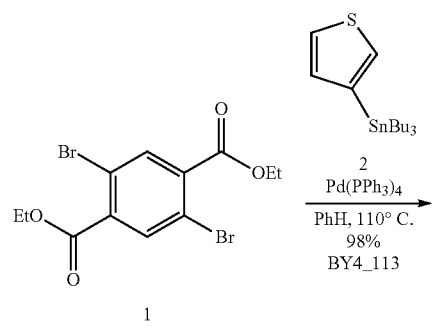

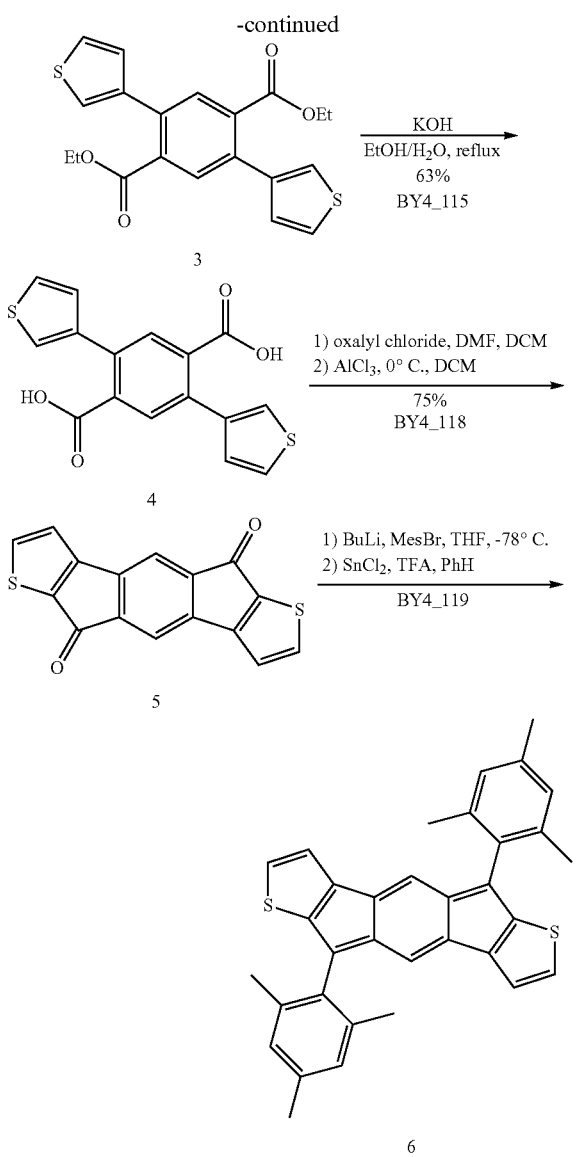

General Procedure A: Stille Cross-Coupling. Bromide 1 (1 equiv) and Pd(PPh$_3$)$_4$ (0.03 equiv) were dissolved in toluene (40 mL) in a screwtop pressure reaction vessel. In a separate flask, stannane (2.4 equiv) was dissolved in toluene (10 mL). Both flasks were sparged with Ar for 40 min, after which the stannane mixture was cannulated into the bromide. The reaction vessel was sealed, heated to 110° C., and stirred for 24-48 hours. The reaction mixture was cooled to rt, filtered through a short pad of silica, and the product purified by column chromatography or recrystallization.

General Procedure B: Ester Hydrolysis. Ester (1 equiv) was suspended in EtOH:H$_2$O (4:1 0.023 M). KOH (16 equiv) was added, and the reaction was stirred at reflux for 16 h. The EtOH was removed under reduced pressure, and the reaction was cooled in an ice bath. Conc. HCl was added to precipitate the resulting carboxylic acid which was collected by vacuum filtration, washed with conc. HCl, H$_2$O, and a small portion of acetone. The solid was then oven-dried and used without further purification.

General Procedure C: Dione Formation. Carboxylic acid (1 equiv) was suspended in dry DCM (0.65 M), and oxalyl chloride (4 equiv) was added followed by dropwise addition of DMF (2 equiv). The reaction was stirred overnight, and the solvent was removed under reduced pressure to give a yellow solid. This solid was redissolved in dry DCM (0.32 M) and cooled in an ice bath. AlCl$_3$ (4.7 equiv) was added, the reaction warmed to rt and stirred overnight. The reaction mixture was poured into an HCl/ice mixture. The resulting precipitate was collected by vacuum filtration, washed with HCl and H$_2$O and oven dried.

General Procedure D: Lithiation/Reduction. Dione (1 equiv) was suspended in dry DCM (30 mL). In a separate flask, mesitylbromide (6 equiv) was dissolved in dry DCM (10 mL). Both flasks were sparged with Ar for 10 min and then cooled to −78° C. BuLi (5 equiv) was added to the mesitylbromide and stirred for 20 min. The resulting lithiated was cannulated into the dione suspension, warmed to rt, and stirred overnight. The reaction was quenched with sat. NH$_4$Cl$_{(aq)}$, extracted with Et$_2$O, dried (MgSO$_4$), and the solvent removed under reduced pressure. The resulting crude diol was dissolved in toluene (40 mL) and sparged with Ar for 20 min. SnCl$_2$ (4 equiv) was added followed by TFA (0.2 mL). The reaction was monitored by TLC and upon completion, filtered through a short pad of Celite. The crude IDT was then purified by recrystalization.

Ester 3. Bromide 1 and stannane 2 were reacted according to General Procedure A.

Purification by column chromatography (1:5 EtOAc:hexanes) gave ester 3 (1.0 g, 98%) as a pale yellow solid: $^1$H NMR (300 MHz, CDCl$_3$) δ 7.80 (s, 2H), 7.38-7.34 (m, 2H), 7.32-7.29 (m, 2H), 7.13 (dd, J=4.8, 1.2 Hz, 2H), 4.19 (q, J=6.9 Hz, 4H), 1.13 (t, J=6.9 Hz, 6H); $^{13}$C NMR (150 MHz, CDCl$_3$) δ 168.18, 140.35, 135.68, 133.78, 131.65, 128.56, 125.53, 123.07, 61.69, 14.04; HRMS (ESI+) for C$_{20}$H$_{18}$O$_4$S$_2$ (M+H)$^+$ calcd 387.0725, found 387.0730.

Carboxylic Acid 4. Ester 3 was reacted according to General Procedure B to give carboxylic acid 4 (0.537 g, 63%) as a white solid: $^1$H NMR (300 MHz, DMSO) δ 13.24 (s, 2H), 7.70 (s, 2H), 7.65 (s, 2H), 7.63-7.60 (m, 2H), 7.21 (dd, J=4.8, 0.9 Hz, 2H); $^{13}$C NMR (150 MHz, DMSO) δ 169.08, 139.54, 133.51, 130.15, 128.16, 126.14, 123.43; HRMS (ESI+) for C$_{16}$H$_{10}$O$_4$S$_2$ (M+H)$^+$ calcd 331.0099, found 331.0089.

Dione 5. Carboxylic acid 4 was reacted according to General Procedure C to give dione 5 (0.333 g, 75%) as a green solid: $^1$H NMR (300 MHz, CDCl$_3$) δ 7.80 (d, J=4.2 Hz, 2H), 7.34 (s, 2H), 7.13 (d, J=4.2 Hz, 2H); $^{13}$C NMR (150 MHz, CDCl$_3$) δ 184.52, 158.07, 142.45, 140.73, 140.37, 136.30, 120.55, 115.68; HRMS (ESI+) for C$_{16}$H$_6$O$_2$S$_2$ (M+H)$^+$ calcd 294.9887, found 294.9896.

Indacenedithiophene (IDT) 6. Dione 5 was reacted according to General Procedure D to give IDT 6 as a blue solid.

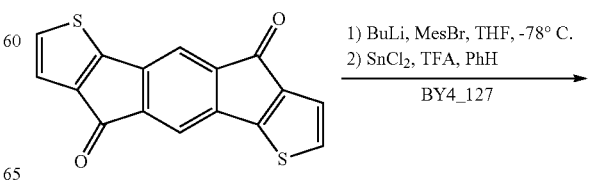

-continued

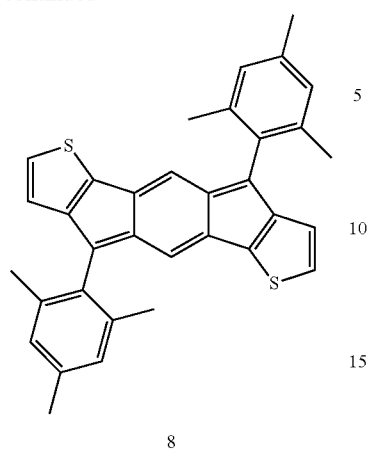

8

IDT 8. Dione 7 was reacted according to General Procedure D to give IDT 8 as a blue solid.

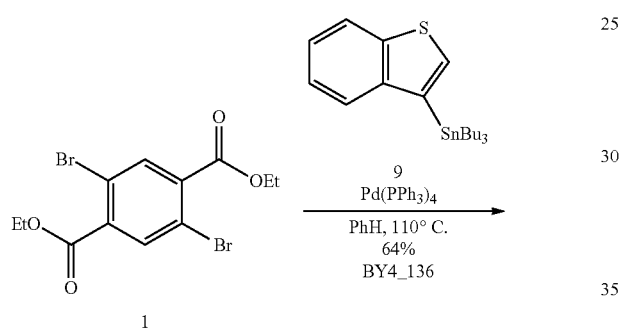

1

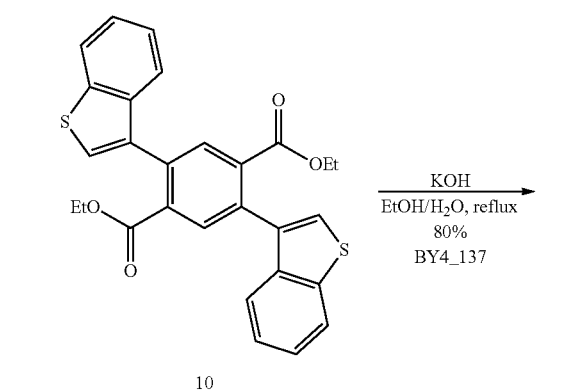

10

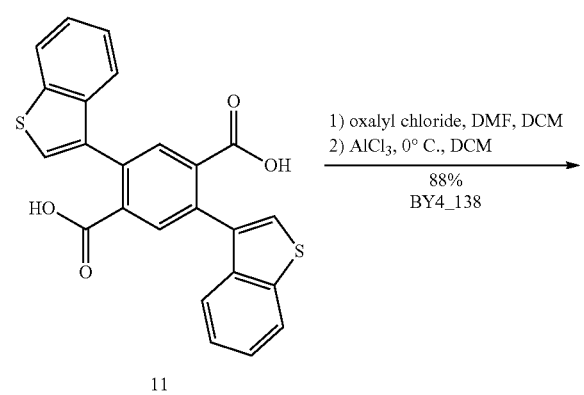

11

-continued

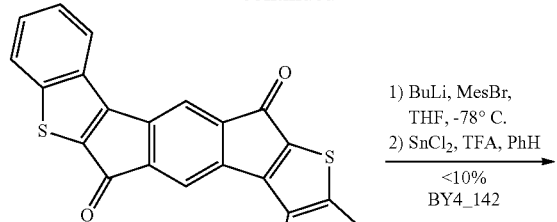

12

13

Ester 10. Bromide 1 and stannane 9 were reacted according to General Procedure A. Recrystallization in DCM/hexanes gave ester 10 (0.825 g, 64%) as a yellow solid: $^1$H NMR (300 MHz, CDCl$_3$) δ 8.06 (s, 2H), 7.94-7.91 (m, 2H), 7.75-7.72 (m, 2H), 7.44 (s, 2H), 7.39-7.35 (m, 4H), 3.91 (q, J=7.2 Hz, 4H), 0.71 (t, J=7.2 Hz, 6H); $^{13}$C NMR (150 MHz, CDCl$_3$) δ 167.29, 139.82, 136.29, 135.69, 134.89, 133.46, 124.71, 124.67, 124.17, 122.98, 1122.53, 61.57, 13.47; HRMS (ESI+) for C$_{28}$H$_{22}$O$_4$S$_2$ (M+H)$^+$ calcd 487.1014, found 487.1024.

Carboxylic Acid 11. Ester 10 was reacted according to General Procedure B to give carboxylic acid 11 (0.373 g, 80%) as a yellow solid: $^1$H NMR (300 MHz, DMSO) δ 13.12 (s, 2H) 8.09-8.06 (m, 2H), 7.91 (s, 2H), 7.84 (s, 2H), 7.54-7.51 (m, 2H), 7.43-7.40 (m, 4H); $^{13}$C NMR (150 MHz, DMSO) δ 167.75, 139.16, 138.39, 135.45, 134.36, 132.44, 125.11, 124.54, 124.42, 123.05, 122.00; HRMS (ESI+) for C$_{24}$H$_{14}$O$_4$S$_2$ (M+H)$^+$ calcd 431.0412, found 431.0420.

Dione 12. Carboxylic acid 11 was reacted according to General Procedure C to give dione 12 (0.404 g, 88%) as a green solid.

IDT 13. Dione 12 was reacted according to General Procedure D to give IDT 13 (5 mg, 10%) as a blue solid: $^1$H NMR (300 MHz, CDCl$_3$) δ 7.76 (d, J=7.5 Hz, 2H), 7.35 (d, J=8.1 Hz, 2H), 7.13-7.01 (m, 6H), 6.97 (s, 4H), 6.02 (s, 2H), 2.41 (s, 12H), 2.36 (s, 6H); $^{13}$C NMR (150 MHz, CDCl$_3$) δ 148.16, 147.07, 146.66, 141.14, 138.19, 137.62, 136.75, 135.05, 133.42, 129.49, 128.64, 125.43, 124.61, 124.51, 124.17, 122.04, 21.41, 20.86.

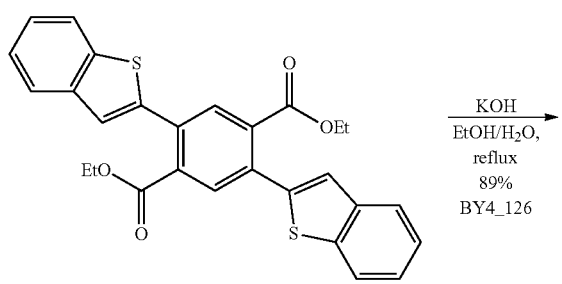

14

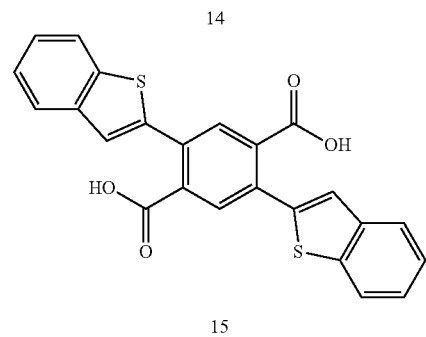

15

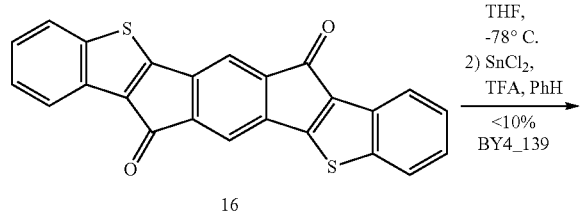

16

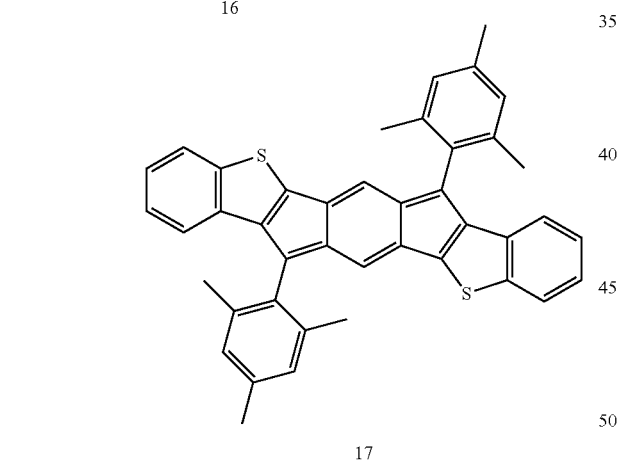

17

(300 MHz, CDCl$_3$) δ 7.47 (d, J=8.1 Hz, 2H), 7.04-6.93 (m, 8H), 6.59 (d, J=8.7 Hz, 2H), 6.07 (s, 2H), 2.38 (s, 6H), 2.33 (s, 12H).

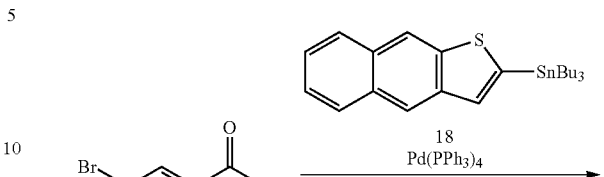

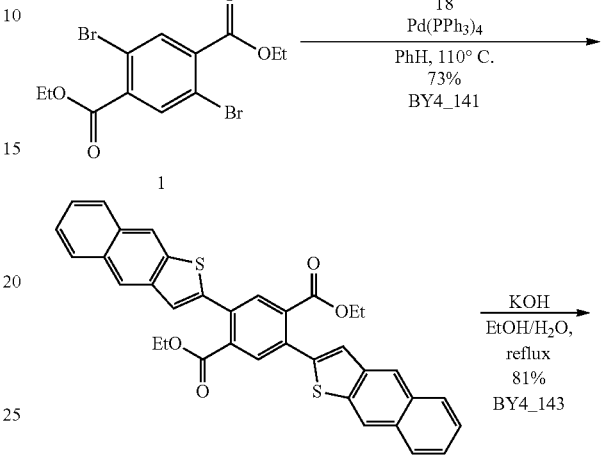

19

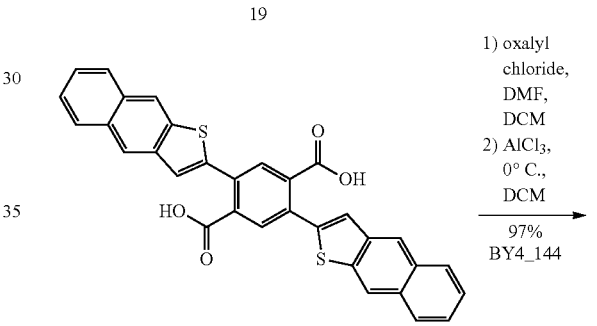

20

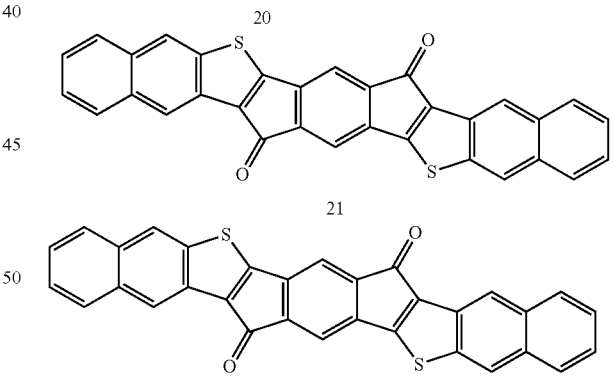

21

Carboxylic Acid 15. Ester 14 was reacted according to General Procedure B to give carboxylic acid 15 (0.783 g, 89%) as a yellow solid: $^1$H NMR (300 MHz, DMSO) δ 13.55 (s, 2H), 8.05-8.02 (m, 2H), 7.93-7.89 (m, 4H), 7.59 (s, 2H), 7.56-7.39 (m 4H); $^{13}$C NMR (150 MHz, DMSO) δ 168.27, 140.04, 139.78, 139.74, 134.99, 132.49, 130.95, 124.88, 124.81, 124.05, 123.82, 122.34; HRMS (ESI+) for C$_{24}$H$_{14}$O$_4$S$_2$ (M+H)$^+$ calcd 431.0412, found 431.0404.

Dione 16. Carboxylic acid 15 was reacted according to General Procedure C to give dione 16 (0.414 g, 75%) as a green solid; HRMS (ESI+) for C$_{24}$H$_{10}$O$_2$S$_2$ (M+H)$^+$ calcd 395.0200, found 395.0216.

IDT 17. Dione 16 was reacted according to General Procedure D to give IDT 17 (5 mg, 10%) as a blue solid: $^1$H NMR Ester 19. Bromide 1 and stannane 18 were reacted according to General Procedure A. Recrystallization in DCM/hexanes gave ester 19 (0.379 g, 73%) as a yellow solid: $^1$H NMR (300 MHz, CDCl$_3$) δ 8.35 (s, 2H), 8.31 (s, 2H), 8.04 (s, 2H), 8.00-7.92 (m, 4H), 7.53-7.46 (m, 4H), 7.43 (s, 2H), 4.24 (q, J=6.9, 4H), 1.06 (t, J=6H); $^{13}$C NMR (150 MHz, CDCl$_3$) δ 167.39, 142.27, 139.41, 138.93, 134.55, 134.53, 134.49, 132.35, 131.34, 128.44, 127.45, 125.71, 125.26, 123.44, 122.34, 120.42, 62.07, 13.94.

Carboxylic Acid 20. Ester 19 was reacted according to General Procedure B to give carboxylic acid 20 (0.270 g, 81%) as a yellow solid: $^1$H NMR (300 MHz, DMSO) δ 8.61

(s, 2H), 8.50 (s, 2H), 8.10-8.00 (m, 6H), 7.72 (s, 2H), 7.57-7.50 (m, 4H); $^{13}$C NMR (150 MHz, DMSO) δ 168.14, 141.54, 139.10, 138.04, 135.04, 132.77, 131.07, 130.76, 130.75, 128.23, 127.24, 125.72, 125.29, 123.48, 122.35, 120.34.

Dione 21. Carboxylic acid 20 was reacted according to General Procedure C to give dione 21 (0.228 g, 97%) as a yellow solid.

Certain embodiments are disclosed herein with reference to the following numbered paragraphs:

1. A compound having a structure of:

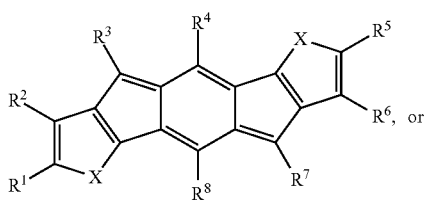

Formula I

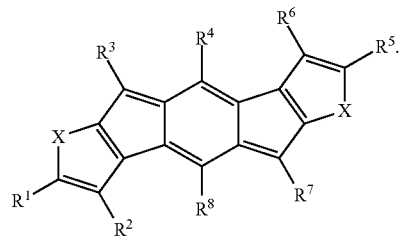

Formula II wherein X is S, SO, SO$_2$, NR$^{10}$, O, or Se;

R$^1$-R$^8$ are each individually H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl, or R$^1$ and R$^2$ together form an aromatic ring and R$^5$ and R$^6$ together form an aromatic ring; and R$^{10}$ is selected from H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl.

2. The compound of paragraph 1, wherein X is S.

3. The compound of paragraph 1 or 2, wherein R$^3$ and R$^7$ are each amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl; and R$^1$, R$^2$, R$^4$, R$^5$, R$^6$ and R$^8$ are each H.

4. The compound of any one of paragraphs 1 to 3, wherein R$^3$ and R$^7$ are each aryl or substituted aryl.

5. The compound of any one of paragraphs 1 to 4, wherein R$^3$ and R$^7$ are each phenyl or substituted phenyl.

6. The compound of any one of paragraphs 1 to 5, wherein R$^3$ and R$^7$ are each phenyl, alkyl-substituted phenyl, alkoxy-substituted phenyl, alkyl- and alkoxy-substituted phenyl, haloalkyl-substituted phenyl, or halo-substituted phenyl.

7. The compound of any one of paragraphs 1 to 6, wherein R$^1$ and R$^5$ are each H, alkyl, alkoxy, or R$^1$ and R$^2$ together form an aromatic ring and R$^5$ and R$^6$ together form an aromatic ring.

8. The compound of any one of paragraphs 1 to 7, wherein R$^2$, R$^4$, R$^6$ and R$^8$ are each H.

9. The compound of any one of paragraphs 1 to 8, wherein the compound has the structure of Formula I.

10. The compound of any one of paragraphs 1 to 8, wherein the compound has the structure of Formula II.

11. An electronic or electrooptical device that includes the compound of claim 1.

12. The device of paragraph 11, wherein the device is an organic light-emitting diode (OLED), an organic field-effect transistor (OFET), or an organic photovoltaic cell (OPV).

13. The device of paragraph 11, wherein the compound of claim 1 is an n-type organic semiconductor.

14. The device of paragraph 11, wherein the device is an organic photovoltaic cell (OPV).

15. The device of paragraph 11, wherein the device is an organic light-emitting diode (OLED), or an organic field-effect transistor (OFET).

In view of the many possible embodiments to which the principles of the disclosed compounds, articles of manufacture, and methods may be applied, it should be recognized that the illustrated embodiments are only preferred examples of the invention and should not be taken as limiting the scope of the invention.

What is claimed is:

1. A compound having a structure of:

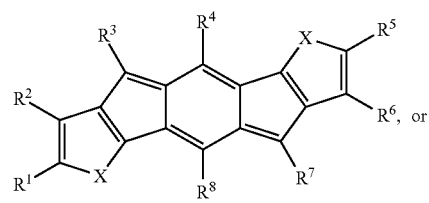

Formula I

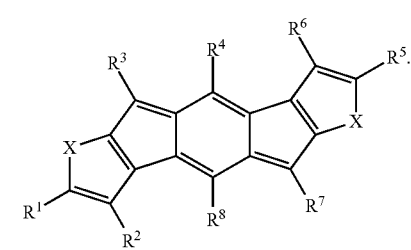

Formula II wherein X is S, SO, SO$_2$, NR$^{10}$, O, or Se;

R$^1$-R$^8$ are each individually H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl, or R$^1$ and R$^2$ together form an aromatic ring and R$^5$ and R$^6$ together form an aromatic ring; and R$^{10}$ is selected from H, amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl.

2. The compound of claim 1, wherein X is S.

3. The compound of claim 1, wherein R$^3$ and R$^7$ are each amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl; and $R^1$, $R^2$, $R^4$, $R^5$, $R^6$ and $R^8$ are each H.

4. The compound of claim 1, wherein $R^3$ and $R^7$ are each aryl or substituted aryl.

5. The compound of claim 1, wherein $R^3$ and $R^7$ are each phenyl or substituted phenyl.

6. The compound of claim 1, wherein $R^1$ and $R^5$ are each H, alkyl, alkoxy, halogen, or $R^1$ and $R^2$ together form an aromatic ring and $R^5$ and $R^6$ together form an aromatic ring.

7. The compound of claim 1, wherein $R^2$, $R^4$, $R^6$ and $R^8$ are each H.

8. The compound of claim 1, wherein the compound has the structure of Formula I.

9. The compound of claim 1, wherein the compound has the structure of Formula II.

10. The compound of claim 1, $R^1$ and $R^2$ together form two or more fused aromatic rings and $R^5$ and $R^6$ together form two or more fused aromatic rings.

11. The compound of claim 1, wherein $R^3$ and $R^7$ are each substituted alkynyl.

12. The compound of claim 2, wherein $R^3$ and $R^7$ are each amino, alkynyl, substituted alkynyl, halogen, alkyl, aryl, substituted alkyl, substituted aryl, nitro, alkoxy, substituted alkoxy, cyano, thiol, substituted thiol, thioether, hydroxyl, heteroaryl, substituted heteroaryl, cycloalkyl, or substituted cycloalkyl; and $R^1$, $R^2$, $R^4$, $R^5$, $R^6$ and $R^8$ are each H.

13. The compound of claim 2, wherein $R^3$ and $R^7$ are each substituted alkynyl, or are each substituted phenyl.

14. The compound of claim 13, wherein $R^3$ and $R^7$ are each alkylsilyl-substituted alkynyl, or are each alkyl-substituted phenyl, or are each haloalkyl-substituted phenyl, or are each halo-substituted phenyl.

15. The compound of claim 3, wherein $R^3$ and $R^7$ are each the same group.

16. The compound of claim 6, wherein $R^1$ and $R^5$ are each the same group.

17. The compound of claim 1, wherein the compound is:

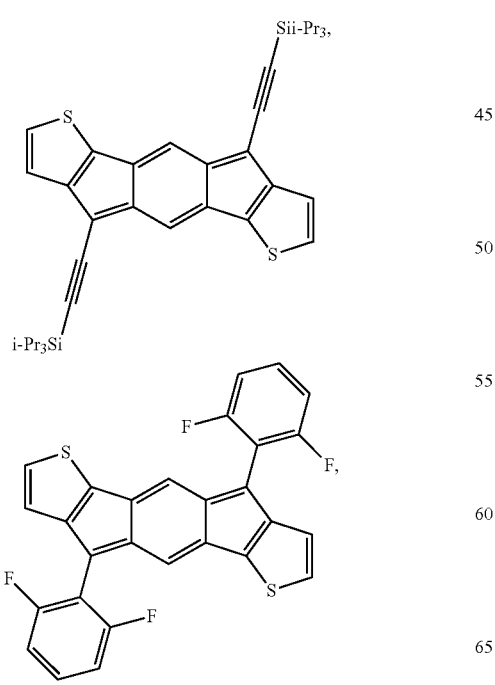

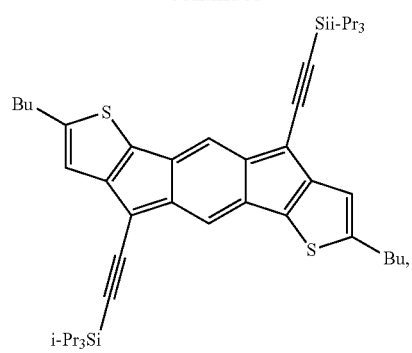

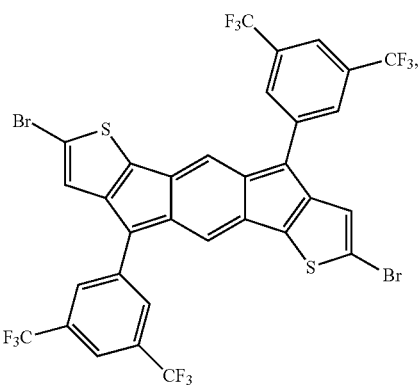

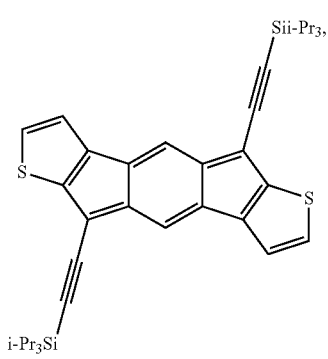

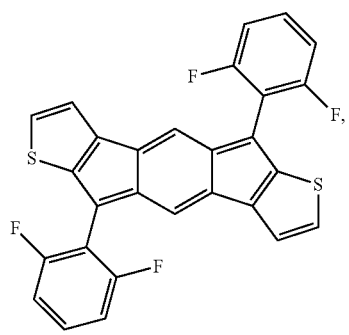

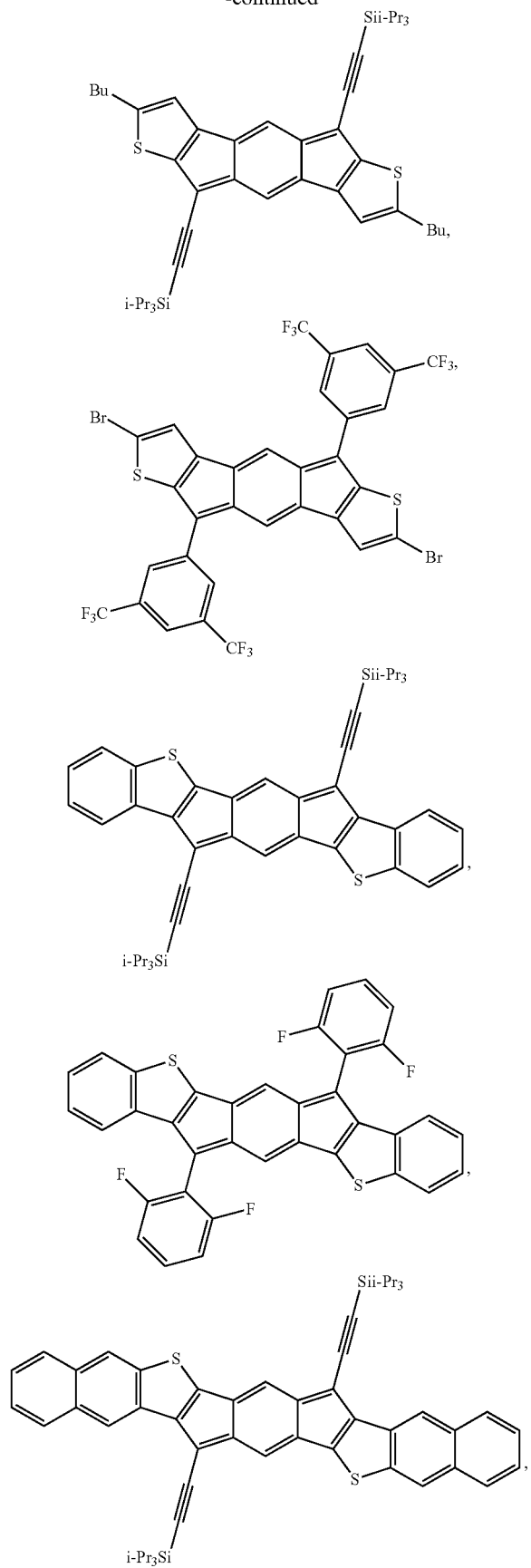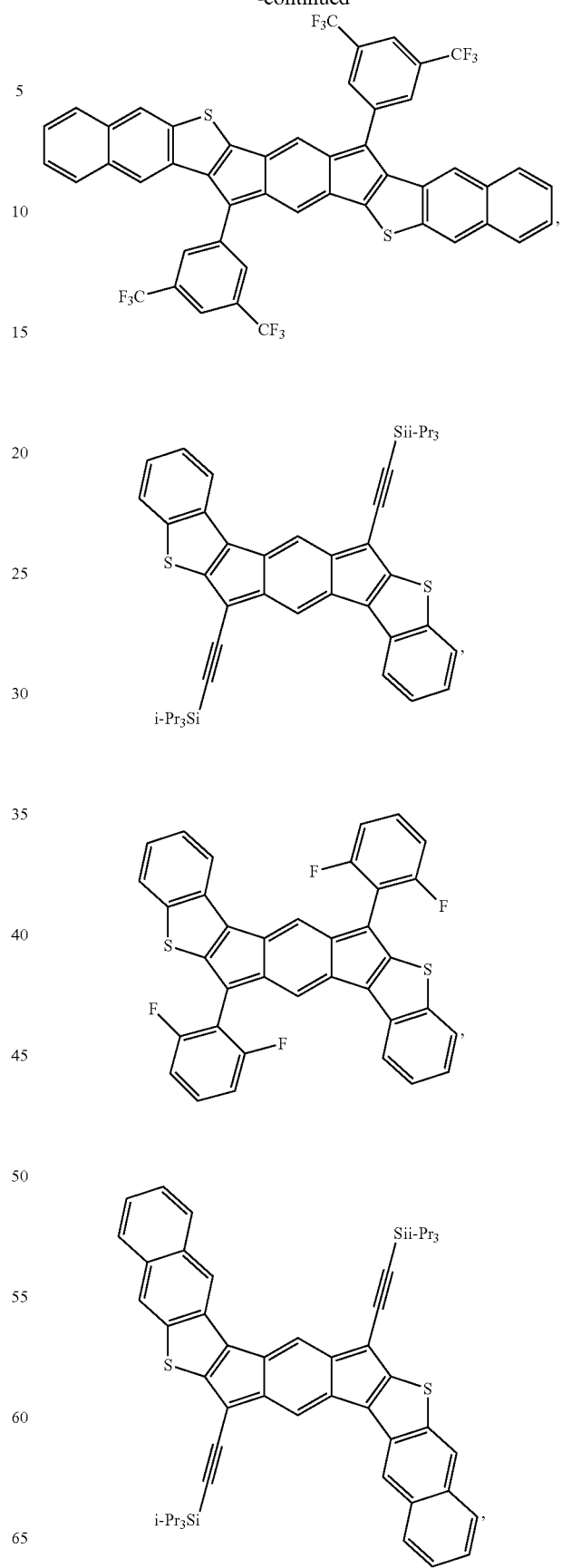

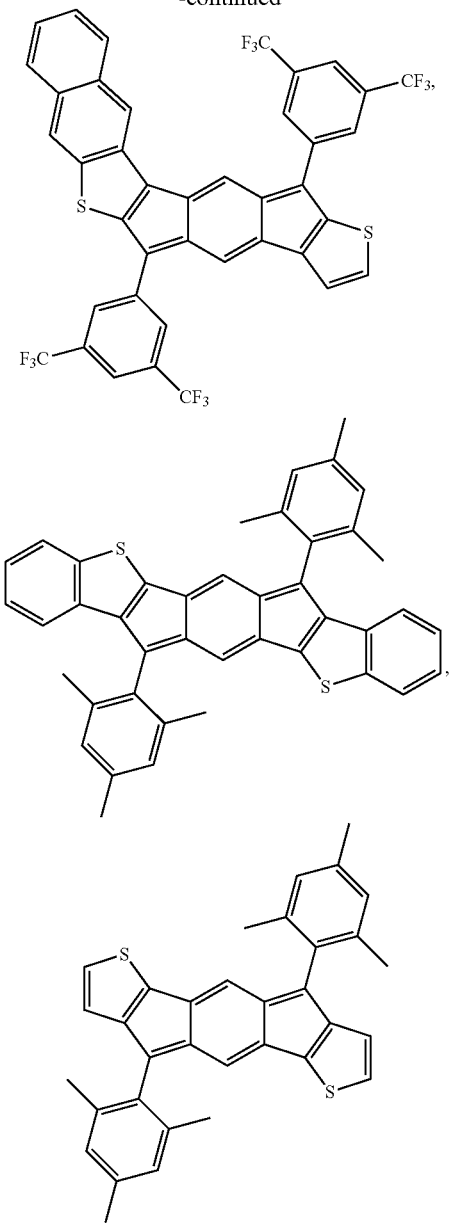

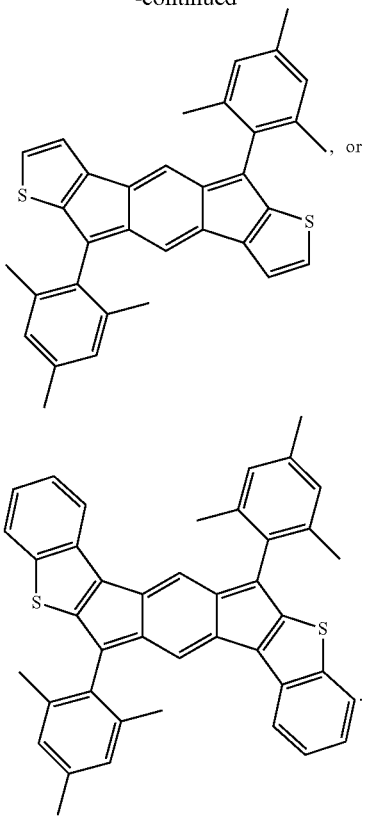

18. An electronic or electrooptical device that includes the compound of claim 1.

19. The device of claim 18, wherein the device is an organic light-emitting diode (OLED), an organic field-effect transistor (OFET), or an organic photovoltaic cell (OPV).

20. The device of claim 18, wherein the compound of claim 1 is an n-type organic semiconductor.

21. The device of claim 18, wherein the device is an organic photovoltaic cell (OPV).

22. The device of claim 18, wherein the device is an organic light-emitting diode (OLED), or an organic field-effect transistor (OFET).

* * * * *